(12) United States Patent
Smith et al.

(10) Patent No.: US 7,806,858 B2
(45) Date of Patent: Oct. 5, 2010

(54) VACUUM ACTUATED SMALL VOLUME SYRINGE

(75) Inventors: Jeffrey Smith, Irvine, CA (US); Rex O. Bare, Lake Forest, CA (US)

(73) Assignee: SafeShot Technologies, LLC, Mission Viejo, CA (US)

( * ) Notice: Subject to any disclaimer, the term of this patent is extended or adjusted under 35 U.S.C. 154(b) by 109 days.

(21) Appl. No.: 11/784,797

(22) Filed: Apr. 10, 2007

(65) Prior Publication Data

US 2007/0260181 A1 Nov. 8, 2007

Related U.S. Application Data

(60) Provisional application No. 60/793,022, filed on Apr. 19, 2006.

(51) Int. Cl.
*A61M 5/00* (2006.01)
*A61M 5/32* (2006.01)

(52) U.S. Cl. .......................... 604/110; 604/198

(58) Field of Classification Search ................ 604/110, 604/192–198

See application file for complete search history.

(56) References Cited

U.S. PATENT DOCUMENTS

| | | | |
|---|---|---|---|
| 4,766,908 A | 8/1988 | Clement | |
| 4,838,869 A | 6/1989 | Allard et al. | |
| 4,950,241 A | 8/1990 | Ranford | |
| 4,966,593 A | 10/1990 | Lennox | |
| 5,019,043 A | 5/1991 | Pastor et al. | |
| 5,085,640 A | 2/1992 | Gibbs | |
| 5,195,985 A | 3/1993 | Hall | |
| 5,211,630 A | 5/1993 | Schmahmann | |
| 5,215,015 A | 6/1993 | Iida et al. | |
| 5,215,533 A | 6/1993 | Robb | |
| 5,226,893 A | 7/1993 | Kayser | |
| 5,334,155 A | 8/1994 | Sobel | |
| 5,336,185 A | 8/1994 | Lynch et al. | |
| 5,344,403 A | 9/1994 | Lee | |
| 5,385,551 A | 1/1995 | Shaw | |
| 5,389,076 A | 2/1995 | Shaw | |
| 5,423,758 A | 6/1995 | Shaw | |
| 5,578,011 A | 11/1996 | Shaw | |
| 5,578,015 A | 11/1996 | Robb | |
| 5,601,534 A | 2/1997 | Turner | |

(Continued)

*Primary Examiner*—Matthew F DeSanto
(74) *Attorney, Agent, or Firm*—Andrew L. Reibman; Louis C. Cullman; K&L Gates, LLP (57) ABSTRACT

A retractable safety syringe is provided herein wherein an external vacuum compartment produces a retraction force which urges a piston of a plunger toward a retracted position. The retractable safety syringe may have a needle holder which is removably engageable to a distal portion of a syringe body. When the piston is traversed toward the engaged position, the external variable vacuum compartment produces a retraction force. When the piston is traversed to an engaged position, the piston engages the needle holder and disengages the needle holder from the syringe body. The medical professional may release a thumb pressure on a thumb platform of a plunger. At this point, the retraction force of the external variable vacuum compartment may traverse the piston along with the needle holder and needle toward the retracted position and into the syringe body. An internal variable vacuum compartment may also create a retraction force to assist retraction of the needle holder and needle into the syringe body.

8 Claims, 3 Drawing Sheets

U.S. PATENT DOCUMENTS

| | | | |
|---|---|---|---|
| 5,632,733 A | 5/1997 | Shaw | |
| 5,658,257 A | 8/1997 | Ryles | |
| 5,681,292 A | 10/1997 | Tober et al. | |
| 5,868,713 A | 2/1999 | Klippenstein | |
| 5,964,735 A | 10/1999 | Alexander | |
| 5,971,964 A | 10/1999 | Donaldson | |
| 6,010,486 A | 1/2000 | Carter et al. | |
| 6,015,438 A | 1/2000 | Shaw | |
| 6,033,385 A | 3/2000 | Liu | |
| 6,036,674 A | 3/2000 | Caizza et al. | |
| 6,050,977 A | 4/2000 | Adams | |
| 6,090,077 A | 7/2000 | Shaw | |
| 6,193,695 B1 | 2/2001 | Rippstein, Jr. | |
| 6,368,303 B1 | 4/2002 | Caizza | |
| 6,413,236 B1 | 7/2002 | Van Dyke | |
| 6,632,198 B2 | 10/2003 | Caizza | |
| 6,712,787 B1 | 3/2004 | Dysarz | |
| 6,752,798 B2 * | 6/2004 | McWethy et al. | 604/506 |
| 6,840,291 B2 | 1/2005 | Caizza et al. | |
| 6,953,449 B2 | 10/2005 | Huang | |
| 6,986,756 B2 | 1/2006 | Pelkey et al. | |
| 7,104,970 B2 | 9/2006 | Chen | |
| 7,118,552 B2 | 10/2006 | Shaw et al. | |
| 7,147,621 B2 | 12/2006 | Kiehne | |
| 7,220,247 B2 | 5/2007 | Shaw et al. | |
| 2001/0053886 A1 | 12/2001 | Caizza | |
| 2002/0193736 A1 | 12/2002 | Kiehne | |
| 2003/0023205 A1 | 1/2003 | Botich et al. | |
| 2003/0212362 A1 | 11/2003 | Roser | |
| 2004/0024357 A1 | 2/2004 | Pelkey et al. | |
| 2004/0116857 A1 | 6/2004 | Kiehne | |
| 2006/0089593 A1 | 4/2006 | Landau et al. | |
| 2006/0089594 A1 | 4/2006 | Landau | |
| 2006/0178625 A1 | 8/2006 | Lim et al. | |
| 2007/0066936 A1 * | 3/2007 | Lam | 604/110 |

* cited by examiner

VACUUM ACTUATED SMALL VOLUME SYRINGE

CROSS-REFERENCE TO RELATED APPLICATIONS

This application claims the benefits of U.S. Provisional Application No. 60/793,022, filed on Apr. 19, 2006, the entire content of which is expressly incorporated herein by reference.

STATEMENT RE: FEDERALLY SPONSORED RESEARCH/DEVELOPMENT

Not Applicable

BACKGROUND

The present invention relates to a small volume (i.e., about 1 cc or less) retractable safety syringe.

In recent years, the public (e.g., drug addicts, drug users, medical personnel and healthcare providers and the like) has become increasingly aware of the health hazards associated with needle reuse and accidental needle prickings. For example, at least twenty blood-borne pathogens may be transmitted by the reuse of needles or accidental needle prickings. For example, these blood borne pathogens may include and are not limited to Human Immunodeficiency Virus (HIV), Acquired Immunodeficiency Syndrome (AIDS), Hepatitis B, Hepatitis C, syphilis, malaria, tuberculosis, and herpes. Despite the awareness of the risk of needle reuse and accidental needle prickings, at least 36 percent of HIV/AIDS cases and more than 50 percent of Hepatitis B and Hepatitis C cases in the United States may be linked to the sharing of needles among drug addicts. Accordingly, there is a need to curb the practice of sharing needles among drug addicts.

The problem of needle sharing or needle reuses is further amplified when viewed in relation to the world population. For example, approximately 30 percent of reported HIV/AIDS cases in Brazil, Chile, Uruguay, Paraguay and Argentina are directly related to the sharing of contaminated needles among drug addicts. Approximately 70 percent of the HIV cases reported in China are directly linked to the sharing of contaminated needles. In eastern European countries, 80 percent of injection drug addicts admit to sharing contaminated needles. Approximately 43 percent of HIV/AIDS cases reported in Poland and Yugoslavia are linked to the sharing of contaminated needles among drug addicts.

Accidental needle prickings also pose a threat to healthcare workers. In particular, approximately one million accidental needle prickings are reported by healthcare workers annually. However, it is believed that at least three million accidental needle prickings occur each year, of which about two million are unreported. Various studies estimate that out of all the accidental needle pricking injuries that occur to nurses, approximately 40 percent to 53 percent go unreported. Various studies also estimate that out of all the needle pricking injuries that occur to laboratory technicians, approximately 92 percent go unreported. Various studies further estimate that out of all the needle pricking injuries that occur to physicians, approximately 70 percent to 95 percent go unreported.

In 1997, the Center for Disease Control and Prevention (CDC) sponsored a study which found that approximately 76 percent of needle pricking injuries could be avoided by using safety needles. Presently, there are at least 250 types of safety syringes. Unfortunately, the safety syringes that currently exist have been criticized for various problems associated in operating the safety syringe and its ineffectiveness.

One type of safety syringe is a vacuum assisted safety syringe wherein the needle of the syringe is retracted into a syringe body after a piston engages a needle holder due to a retraction force of a variable vacuum compartment. The retraction force of the variable vacuum compartment is a function of the size and volume of the variable vacuum compartment as the plunger is traversed from a retracted position to an engaged position. If the variable vacuum compartment is not sufficiently large, then the retraction force of the variable vacuum compartment may not be sufficient to withdraw the needle holder and needle into the syringe body. This problem is particularly pronounced when the retractable safety syringe has a small variable fluid chamber of about 1 cc or less. Small variable fluid chambers require a syringe body having a small diameter. Correspondingly, the variable vacuum compartment is also small limiting its maximum potential retraction force. If the retraction force of the variable vacuum compartment is not greater than a force required to traverse the needle holder and needle into the safety syringe, then the needle will still be exposed outside of the syringe body thereby possibly pricking a medical professional or allowing a drug addict to reuse the needle.

Accordingly, there is a need in the art for an improved safety syringe.

BRIEF SUMMARY

The retractable safety syringe discussed herein resolves the issues discussed above, discussed below and those that are known in the art.

The retractable safety syringe may have a syringe body, plunger, needle holder and needle. The plunger which may comprise a piston and a rigid shaft may be disposed within the syringe body. The needle may be attached to the needle holder. Also, the needle holder may be removeably engageable to the syringe body. The volume defined by the needle holder, syringe body and the piston may be referred to as a variable fluid chamber. On the opposed side of the piston within the syringe body is an internal variable vacuum compartment. The internal variable vacuum compartment may be defined by the piston, syringe body and a proximal seal through which the rigid shaft extends. The piston forms an airtight and fluid tight seal with the syringe body. Also, the proximal seal may form an airtight seal between the syringe body and the rigid shaft. When the piston is traversed toward an engaged position, no air molecules are introduced into the internal variable vacuum compartment thereby producing a retraction force urging the piston back toward a retracted position.

The syringe may also have an external variable vacuum compartment which also produces a retraction force urging the piston back toward the retracted position when the piston is traversed toward the engaged position. The external variable vacuum compartment may be defined by a rigid shell, the syringe body, proximal seal and a shell seal. The rigid shell may be disposed over the syringe body. A distal portion of the rigid shell may have the shell seal which provides an airtight seal between the rigid shell and the syringe body. The proximal seal may provide an airtight seal between the proximal portion of the syringe body and the rigid shell. When the piston is traversed toward the engaged position, the external variable vacuum compartment is increased in volume without any addition of air molecules thereby producing a retraction force. The retraction force of the external variable vacuum compartment urges the piston back toward the retracted position.

It is contemplated that the piston may be urged back toward the retracted position by the retraction force created by the external variable vacuum compartment. Also, the piston may be urged back toward the retracted position by the retraction forces created by the external variable vacuum compartment and another mechanism (e.g., spring, etc.). As a further alternative, it is contemplated that the piston may be urged back toward the retracted position by the retraction forces created by both the external and internal variable vacuum compartments.

The piston may be engageable to the needle holder when the piston is traversed to the engaged position. By way of example and not limitation, the piston may be formed with longitudinal offset tabs that engage a flange of the needle holder.

In use, the safety syringe may be provided to the medical professional with fluidic medication filled in the variable fluid chamber. To inject a patient, the medical professional may invert the syringe such that the needle is pointing upward. The medical professional may tap the syringe to dislodge any air bubbles within the variable fluid chamber toward the needle. The piston is slightly traversed toward the engaged position to remove the trapped air bubbles within the variable fluid chamber. The external and internal variable vacuum compartments produces retraction forces which urge the piston back toward the retracted position. Accordingly, the medical professional maintains thumb pressure on a thumb platform to prevent reintroducing air into the variable fluid chamber.

The medical professional injects the fluid medication into the patient by traversing the piston to the engaged position. At the engaged position, the piston engages the needle holder and the needle holder is disengaged from the syringe body. The medical professional may remove his/her thumb pressure from the thumb platform such that the retraction forces of the external and internal variable vacuum compartments urge the piston, needle holder and needle into the syringe body. Once the needle is withdrawn into the syringe body, the needle may be canted toward one side of the syringe body. The syringe cannot be reused thus preventing accidental needle pricking and reuse of the syringe.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
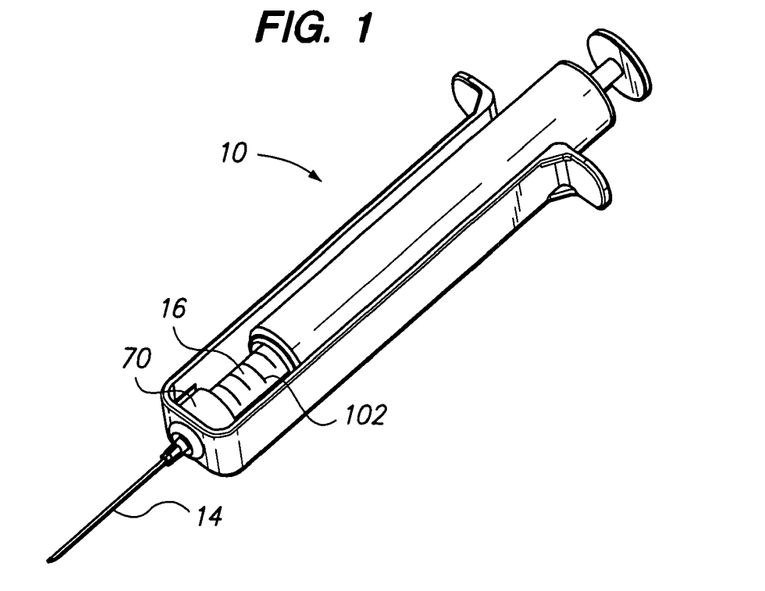
FIG. 1 is a perspective view of a retractable safety syringe.

Referring now to the drawings which are for the purposes of illustrating the preferred embodiments of a retractable safety syringe 10 and not for the purpose of limiting the same, FIG. 1 is a perspective view of the retractable safety syringe 10 with an external variable vacuum compartment 12 (see FIG. 2) for creating a retraction force to retract a needle 14 of the retractable safety syringe 10 within the retractable safety syringe 10 so as to prevent accidental needle pricking and needle reuse. Although the discussion provided herein regarding the retractable safety syringe 10 is made in relation to small volume syringes (i.e., about 1 cc or less), it is also contemplated that the various aspects of the retractable safety syringe 10 may also be variously embodied and employed in large volume safety syringes (i.e., 1 cc or more).

The retractable safety syringe 10 may comprise a syringe body 16 defining a distal portion and a proximal portion. A needle holder 18 may be removably engaged to the distal portion of the syringe body 16. Also, a needle 14 may be fixedly engaged to the needle holder 18 and protrude coaxially out of the syringe body 16. The retractable safety syringe 10 may also comprise a plunger 20 having a piston 22 traversable within the syringe body 16 between a retracted position and an engaged position. The plunger 20 may also comprise a rigid shaft 24 disposed within the syringe body 16 and engaged to the piston 22. The rigid shaft 24 may extend out of the syringe body 16 through the proximal portion of the syringe body 16 and may be coaxially aligned with the syringe body 16. A thumb platform 26 may be attached to the proximal portion of the rigid shaft 24. Also, the thumb platform 26 may be operative to traverse the piston 22 between the retracted position and the engaged position. The plunger 20 may also comprise a rigid shell 28 engaged to the proximal portion of the rigid shaft 24. The rigid shell 28 may extend over the syringe body 16 and terminate at about the distal portion of the rigid shaft 24 or the piston 22. A proximal seal 30 may be interposed between the proximal portion of the syringe body 16 and the inner surface 32 of the rigid shell 28. The proximal seal 30 forms an air tight seal between the syringe body 16 and the rigid shell 28. A shell seal 34 may be disposed on the distal portion of the rigid shell 28 and be engaged to the outer surface 36 of the syringe body 16.

The volume defined by the proximal seal 30, shell seal 34, rigid shell 28 and syringe body 16 defines a first variable vacuum compartment or an external variable vacuum compartment 12. In use, the external variable vacuum compartment 12 produces a retraction force that urges the plunger 20 toward the retracted position when the piston 22 is traversed toward the engaged position. For example, when the medical professional injects the patient with the fluidic medication, the piston 22 is traversed to the engaged position. At this point, the piston 22 engages the needle holder 18. When the medical professional releases the thumb platform 26, the retraction force of the external variable vacuum compartment 12 urges the piston 22 as well as the needle holder 18 and needle 14 toward the retracted position. The needle 14 is withdrawn into the syringe body 16 and is no longer exposed such that there is no risk of accidental needle pricking and the needle 14 may not be reused.

The retractable safety syringe 10 may comprise the needle 14, needle holder 18, syringe body 16, plunger 20, and a carriage 38. The syringe body 16, plunger 20 and carriage 38 may be generally coaxially aligned with each other such that the plunger 20 (i.e., rigid shell 28 and piston 22) may be slidably traversable between the carriage 38 and the syringe body 16 and within the syringe body 16. The carriage 38 may have a U-shaped configuration (see FIG. 1), as discussed in detail below, a generally cylindrical configuration (not shown) or other configuration. The carriage 38 may define an inner cavity 40. The syringe body 16 may reside or be disposed within the inner cavity 40 of the carriage 38. The carriage 38 may define a distal portion and a proximal portion. The distal portion may have a rounded configuration and extend radially inward. The distal portion of the carriage 38 may be fixedly engaged to the distal portion of the syringe body 16. By way of example and not limitation, the distal portion of the carriage 38 may be fixedly engaged to the distal portion of the syringe body 16 via sonic welding, adhesive, or other temporary or permanent joining methods.

Figure 5:
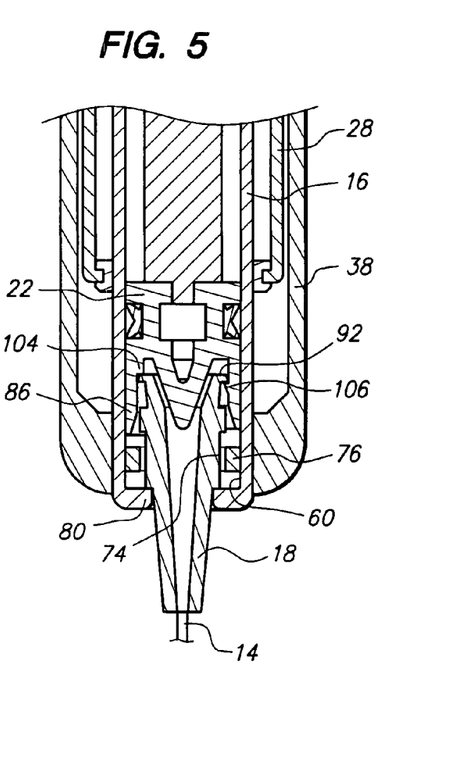
FIG. 5 is an enlarged cross sectional view of the distal portion of the syringe with the piston disposed at an engaged position.

The syringe body 16 may have a generally cylindrical configuration. An inner volume of the syringe body 16 may contain the piston 22, rigid shaft 24 and the needle holder 18. Preferably, the rigid shaft 24 is fixedly engaged to the piston 22. The piston 22 is traversable between the engaged position and the retracted position. At the engaged position, the piston 22 is disposed adjacent the distal portion of the syringe body 16 and engaged to the needle holder 18, as shown in FIG. 5. At the retracted position, the piston 22 is generally disposed adjacent the proximal portion of the syringe body 16. The rigid shaft 24 extends through the proximal portion of the syringe body 16. A proximal portion of the rigid shaft 24 is disposed external to the syringe body 16. A thumb platform 26 may be engaged to the proximal portion of the rigid shaft 24. The piston 22 may be traversable between the engaged position and the retracted position by pushing or pulling the thumb platform 26 in relation to the syringe body 16. The thumb platform 26 may have a generally circular disc configuration. The thumb platform 26 may be sufficiently large to provide thumb support to the thumb of the medical professional as the medical professional depresses the thumb platform 26 to traverse the piston 22 toward the engaged position. Also, the thumb platform 26 may have an underside surface 42 which may be sufficiently large such that the medical professional may grasp the thumb platform 26 with his/her fingers to pull the thumb platform 26 to traverse the piston 22 toward the retracted position.

The plunger 20 may also comprise a rigid shell 28 having a cylindrical configuration. Other configurations are also contemplated such as square, pentagonal, oval, etc. The rigid shell 28 may be interposed between the carriage 38 and the syringe body 16. The rigid shell 28 may define an open distal portion and a partially open proximal portion. The distal portion of the rigid shell 28 may have an inwardly directed flange 44. A shell seal 34 may be disposed about an inner periphery of the inwardly directed flange 44 of the rigid shell distal portion. The shell seal 34 may also be slidingly engageable with an outer surface 36 of the syringe body 16. The shell seal 34 may provide an airtight seal between the rigid shell 28 and the syringe body 16. More particularly, the shell seal 34 may provide an airtight seal between the distal portion of the rigid shell 28 and the outer surface 36 of the syringe body 16. In use, as the piston 22 is traversed between the engaged position and the retracted position, the shell seal 34 slides on the outer surface 36 of the syringe body 16 between the proximal portion and the distal portion of the syringe body 16.

The proximal portion of the syringe body 16 may have an outwardly directed flange 46. A proximal seal 30 may be disposed about an outer periphery of the outwardly directed flange 46 of the syringe body 16 proximal portion. The proximal seal 30 may also slidingly engage the inner surface 32 of the rigid shell 28. The proximal seal 30 may form an airtight seal between the syringe body 16 and the rigid shell 28. More particularly, the proximal seal 30 may provide an airtight seal between the proximal portion of the syringe body 16 and the inner surface 32 of the rigid shell 28. The proximal seal 30 may provide the airtight seal against the inner surface 32 of the rigid shell 28 as the piston 22 is traversed between the engaged position and the retracted position.

The first variable vacuum compartment or the external variable vacuum compartment 12 defined by the proximal seal 30, shell seal 34, syringe body 16 and rigid shell 28 increases in volume as the plunger 20 is traversed toward the engaged position. Conversely, the external variable vacuum compartment 12 decreases in volume as the plunger 20 is traversed toward the retracted position. Initially, the safety syringe 10 may be provided to the medical professional with the plunger 20 in the retracted position. When the medical professional depresses the thumb platform 26 to traverse the piston 22 toward the engaged position, the external variable vacuum compartment 12 increases in volume without any additional air molecules being introduced into the external variable vacuum compartment 12. A vacuum is created in the external variable vacuum compartment 12 when the plunger 20 is traversed toward the engaged position producing a retraction force which urges the plunger 20 toward the retracted position.

The proximal portion of the syringe body 16, rigid shaft 24, and rigid shell 28 defines a proximal compartment 48. The proximal compartment 48 does not have a vacuum when the plunger 20 is traversed toward the retracted position because as the plunger 20 is traversed toward the retracted position, air molecules from the environment is introduced into the proximal compartment 48 through an air vent 50. Also, the proximal compartment 48 does not compress air when the piston 22 is traversed toward the engaged position because as the plunger 20 is traversed to the engaged position, air molecules within the proximal compartment 48 may escape out of the proximal compartment through the air vent 50. As such, as the plunger 20 is traversed between the engaged position and the retracted position, the proximal compartment does not produce a retraction force which urges the plunger 20 toward the retracted position or an extension force which urges the plunger 20 toward the extended position.

As discussed above, the proximal seal 30 engages the proximal portion of the syringe body 16 and slidingly engages the inner surface 32 of the rigid shell 28. Additionally, the proximal seal 30 may extend from the proximal portion of the syringe body 16 and slidingly engage the outer surface 54 of the rigid shaft 24 of the plunger 20. The proximal seal 30 may provide an airtight seal between the rigid shaft 24 of the plunger 20 and the syringe body 16. More particularly, the proximal seal 30 may provide an airtight seal between the proximal portion of the syringe body 16 and an outer surface 54 of the rigid shaft 24 of the plunger 20. Also, a piston seal 56 may be disposed about an outer periphery of the piston 22 which provides an airtight and fluid tight seal between the piston 22 and the syringe body 16. More particularly, the piston seal 56 may be disposed within an undercut groove 58 of the piston 22 formed about an outer diameter of the piston 22. The piston seal 56 may be slidingly engaged to the inner surface 60 of the syringe body 16. As the piston 22 is traversed toward the retracted position and toward the engaged position, the piston seal 56 slides along the inner surface 60 of the syringe body 16 and may have an airtight seal and a fluid tight seal against the inner surface 60 of the syringe body 16. Also, the proximal seal 30 may slide against the outer surface 54 of the rigid shaft 24 of the plunger 20 as the plunger 20 is traversed between the retracted position and the engaged position.

The proximal seal 30, the piston seal 56, syringe body 16 and rigid shaft 24 may define a second variable vacuum compartment or an internal variable vacuum compartment 62. Initially, when the retractable safety syringe 10 is provided to the medical professional, the plunger 20 may be in the retracted position. As the plunger 20 is traversed toward the engaged position, the internal variable vacuum compartment 62 may increase in volume. Also, since the piston seal 56 and proximal seal 30 create an airtight seal between the syringe body 16 and the rigid shaft 24, a vacuum is formed in the internal variable vacuum compartment 62. The vacuum produces a retraction force which urges the plunger 20 and piston 22 toward the retracted position as the plunger 20 is traversed toward the engaged position.

In use, when the plunger 20 is traversed to the engaged position, the piston 22 of the plunger 20 engages the needle holder 18. The retraction force of the external variable vacuum compartment 12 and the internal variable vacuum compartment 62 traverses the piston 22 as well as the needle holder 18 and needle 14 into the syringe body 16. The retraction force of the external variable vacuum compartment 12 may be increased by increasing the inner diameter 64 of the rigid shell 28 over the outer diameter 66 of the syringe body 16. As the inner diameter 64 of the rigid shell 28 increases over the outer diameter 66 of the syringe body 16, the volume of the external variable vacuum compartment 12 measured when the plunger 20 is at the engaged position increases. The increased volume creates a larger retraction force. With respect to the internal variable vacuum compartment 62, the retraction force of the internal variable vacuum compartment 62 may be increased by reducing the outer diameter of the rigid shaft 24 or increasing the inner diameter of the syringe body 16. As such, when the plunger 20 is traversed to the engaged position, the internal variable vacuum compartment 62 is also increased thereby producing a greater retraction force.

It is contemplated that the proximal seal 30 may engage the proximal portion of the syringe body 16 and only the shell (i.e., inner surface 32 of the shell 28) to form the external variable vacuum compartment 12. No internal variable vacuum compartment is formed. In this instance, the external variable vacuum compartment 12 is sized to provide a sufficient retraction force to withdraw the needle 14 into the syringe body 16 after the piston 22 has engaged the needle holder 18. Alternatively, it is contemplated that the proximal seal 30 may engage the proximal portion of the syringe body 16 and both the rigid shell 28 and the shaft of the plunger 20 (see portion 52 in FIG. 2), and more particular, the inner surface 32 of the shell 28 and the outer surface 54 of the shaft 24. In this instance, the external and internal variable vacuum compartments 12, 62 are sized to provide sufficient retraction forces to withdraw the needle 14 into the syringe body 16 after the piston 22 has engaged the needle holder 18.

Figure 2:
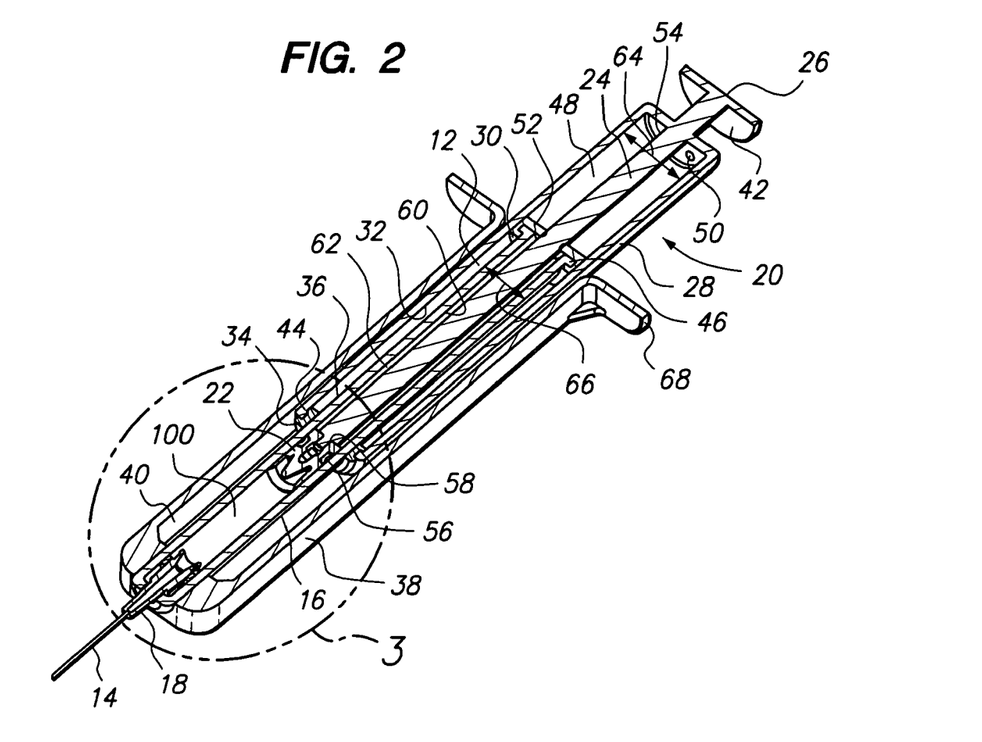
FIG. 2 is a cross sectional perspective view of the syringe shown in FIG. 1.

The carriage 38 may have a U-shaped configuration, as shown in FIGS. 1 and 2. The carriage 38 may define a proximal portion and a distal portion. The carriage 38 may have finger platforms 68 formed on the proximal portion of the carriage 38. The finger platforms 68 are operative to provide leverage such that the medical professional may push or pull the plunger 20 with respect to the syringe body 16. The distal portion of the carriage 38 may have a flat bottom configuration with an aperture formed therethrough. The flat bottom may also have a cap 70 (see FIG. 1) for receiving a distal portion of the syringe body 16. The cap 70 may be fixedly engaged to the distal portion of the syringe body 16 via sonic welding, adhering, friction fit, and other methods known in the art. Throughout the operation of the retractable safety syringe 10, the distal portion of the syringe body 16 may be fixedly engaged to the distal portion of the carriage 38. Also, a proximal portion of the carriage 38 may have an optional bridge which connects proximal portions of tines of the carriage 38. The bridges prevent the proximal portions of the carriage tines from compressing onto the outer surface of the rigid shell 28 thereby creating friction between the carriage 38 and the rigid shell 28. Such friction may prevent the retraction forces of the internal variable vacuum compartment 62 and/or the external variable vacuum compartment 12 from retracting the needle holder 18 and needle 14 into the syringe body 16.

Figure 3:
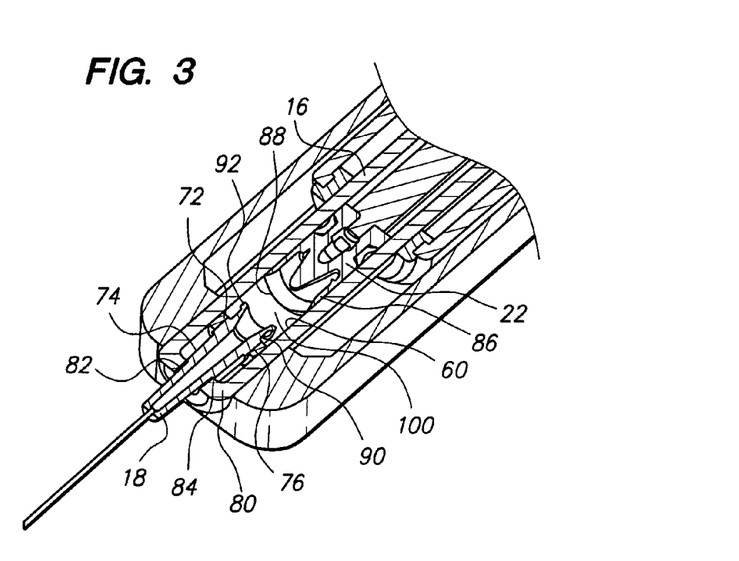
FIG. 3 is an enlarged cross sectional perspective view of a distal portion of the syringe shown in FIG. 2.
Figure 4:
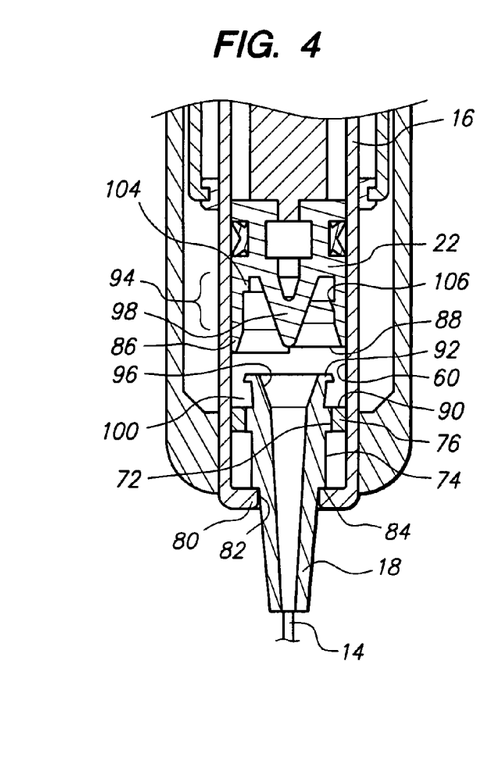
FIG. 4 is an enlarged cross sectional view of the distal portion of the syringe with a piston disposed at a filling position.

The needle holder 18 may be removeably engageable to the distal portion of the syringe body 16. In particular, the needle holder 18 may have a retaining surface 72 and a releasing surface 74, as shown in FIGS. 3-5. The retaining surface 72 may be disposed immediately above the releasing surface 74. The retaining surface 72 may have an outer diameter which is larger than the releasing surface 74. Initially, when the needle holder 18 is engaged to the syringe body 16, a retaining member 76 may be interposed between the retaining surface 72 and the inner surface 60 of the syringe body 16. The retaining member 76 may frictionally engage the inner surface 60 of the syringe body 16 and may also frictionally engage the retaining surface 72 of the needle holder 18.

The retaining member 76 may be disposed about the retaining surface 72 or the releasing surface 74. When the retaining member 76 is disposed about the retaining surface 72, the retaining member 76 is in a first position. When the retaining member 76 is disposed about the releasing surface 74, the retaining member 76 is in a second position. When the retaining member 76 is disposed about the releasing surface 74 (see FIG. 5), the retaining member 76 may frictionally engage the inner surface 60 of the syringe body 16 but may be disengaged from the releasing surface 74. As such, the needle holder 18 may be retracted into the syringe body 16 under the retraction forces of the external and/or internal variable vacuum compartments 12, 62. When the retaining member 76 is disposed about the retaining surface 72 (see FIG. 4), the retaining member 76 may provide a fluidic seal between the needle holder 18 and the syringe body 16.

The distal portion of the syringe body 16 may have an inwardly directed flange 80 and a through hole may be formed through the distal portion of the syringe body 16. The needle holder 18 may be partially disposed within the syringe body 16 and also extend through the aperture of the distal portion of the syringe body 16. An inner diameter of the aperture of the distal portion of the syringe body 16 may be about equal to an outer diameter of a holding surface 82 of the needle holder 18. The junction between the holding surface 82 and the releasing surface 74 may define a lip 84 which abuts the inwardly directed flange 80 of the syringe body 16. As discussed above, the retaining member 76 may be traversed from the first position to the second position. When the retaining member 76 is traversed to the second position from the first position, the needle holder 18 is urged downwardly due to frictional forces. The lip 84 and the inwardly directed flange 80 of the distal portion of the syringe body 16 contact each other and provide a resisting force to prevent downward movement of the needle holder 18.

To traverse the retaining member 76 from the first position to the second position, the piston 22 may be formed with a punch 86. The punch 86 may be formed on the distal portion of the piston 22. The punch 86 may have a cylindrical configuration and be sized and configured to mate with the retaining member 76. More particularly, the punch 86 may have a lower surface 88 which mates with an upper surface 90 of the retaining member 76. When the piston 22 is traversed toward the engaged position, the lower surface 88 of the punch 86 contacts the upper surface 90 of the retaining member 76. When the piston 22 is further traversed to the engaged position, the punch 86 creates a force greater than the frictionally forces between the retaining member 76 with the syringe body 16 and retaining surface 72 of the needle holder 18. The punch 86 of the piston 22 displaces the retaining member 76 from the first position to the second position. Also, the lip 84 contacts the inwardly directed flange 80 of the syringe body 16 distal portion and prevents the needle holder 18 from being pushed out of the syringe body 16.

Figure 6:
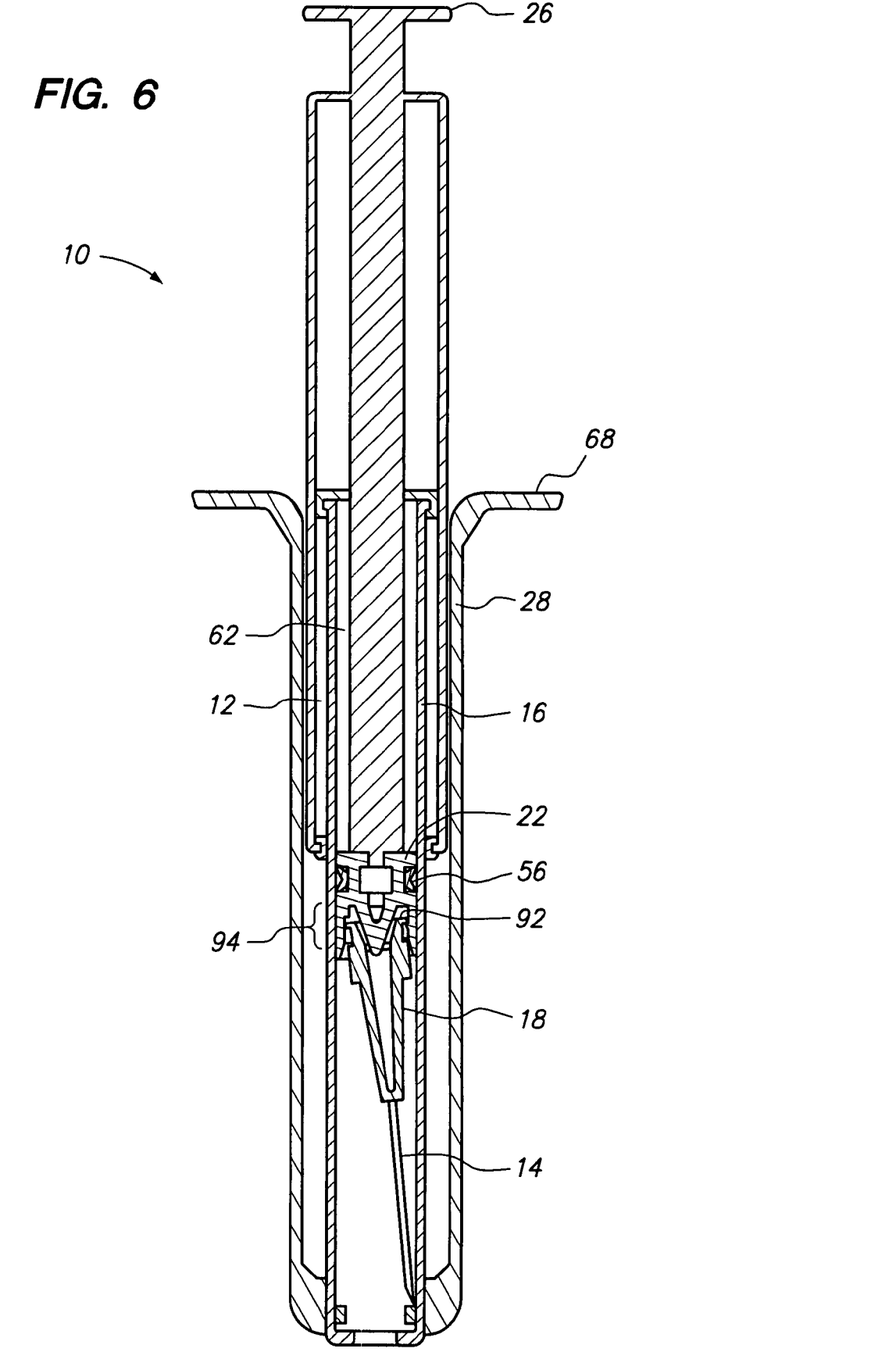
FIG. 6 is a front cross sectional view of the syringe with a needle of the syringe retracted into a syringe body and canted toward one side of the body.

At about the moment that the retaining member 76 is traversed from the first position to the second position, the piston 22 engages the needle holder 18 (see FIG. 5). In particular, the proximal portion of the needle holder 18 may have an outwardly directed flange 92. Also, the piston 22 may have longitudinal offset tabs 94 which engage the needle holder 18, and more particularly, the outwardly directed flange 92 of the needle holder 18. The engagement between the outwardly directed flange 92 and the longitudinal offset tabs 94 is discussed in more detail in U.S. Pat. No. 6,413,236, issued to Van Dyke, the entire content of which is expressly incorporated herein by reference. The longitudinal offset tabs 94 engage the outwardly directed flange 92 of the needle holder 18 such that when the piston 22 is withdrawn into the syringe body 16 via the retraction force, the needle 14 is also canted toward one side of the syringe body 16, as shown in FIG. 6. In particular, the longitudinal offset tabs 94 may comprise an upper proximal block tab 104 and a lower distal wedge tab 106 (see FIG. 4). The lower distal wedge tab 106 passes and hooks onto the flange of the needle holder 18 when the piston 22 is traversed to the engaged position (see FIG. 5). The upper proximal block tab 104 does not pass the outwardly directed flange 92 of the needle holder 18 when the piston 22 is traversed to the engaged position (see FIG. 5). Rather, the upper proximal block tab 104 pushes down on the outwardly directed flange 92 of the needle holder 18. When the needle 14 and needle holder 18 are retracted into the syringe body 16, the upper proximal block tab 104 pushes down on the outwardly directed flange 92 of the needle holder 18 and the lower distal wedge tab 106 pulls up on the outwardly directed flange 92 of the needle holder 18 to cant the needle 14 to one side of the syringe (see FIG. 6).

The needle holder 18 may also have a proximally facing frust conical surface 96 (see FIG. 4). Also, the piston 22 may have a frusto conical cone 98 protruding out of a distal portion of the piston 22. The frusto conical cone 98 may mate with the frust conical surface 96 when the piston 22 is traversed to the engaged position to eject as much fluidic medication out of a variable fluid chamber 100. The variable fluid chamber 100 is the volume defined by the needle holder 18, piston 22 and syringe body 16.

Although the retractable safety syringe 10 discussed herein is in relation to small volume safety syringe having a variable fluid chamber 100 sized at about 1 cc or less, the external variable vacuum compartment 12 may be employed and embodied on the retractable safety syringes on large retractable safety syringes having a variable fluid chamber 100 sized greater than 1 cc or more.

In use, the retractable safety syringe 10 may be provided to medical professionals with fluidic medication pre-filled in the variable fluid chamber 100. If the variable fluid chamber 100 is filled/pre-filled with fluidic medication, then the retractable safety syringe 10 is provided to the medical professional with the plunger 20 in the retracted position. In this state, the external variable vacuum compartment 12 and/or internal variable vacuum compartment 62 does not produce a retraction force which urges the plunger 20 toward the retracted position. To inject the fluidic medication into the patient, the medical professional may invert the retractable safety syringe 10 such that the needle 14 is pointed upward. The medical professional may tap the carriage 38 or the retractable safety syringe 10 to dislodge any air bubbles within the variable fluid chamber 100 toward the needle 14. The medical professional may slightly depress the thumb platform 26 to eject the air bubbles out of the variable fluid chamber 100. The medical professional may maintain thumb pressure on the thumb platform 26 such that the piston 22 does not traverse back toward the retracted position and reintroduce air into the variable fluid chamber 100.

The medical professional then inserts the needle 14 into the body of the patient. After insertion, the medical professional depresses the thumb platform 26 to traverse the piston 22 toward the engaged position. As the piston 22 is traversed toward the engaged position, the internal and/or external variable vacuum compartments 62, 12 increase in volume without any additional air molecules being introduced into the external and/or internal variable vacuum compartments 12, 62. A vacuum is created in the external and/or internal variable vacuum compartments 12, 62 which produce retraction forces which urge the plunger 20 and piston 22 back toward the retracted position. As long as the thumb of the medical professional applies pressure to the platform, the piston 22 is not traversed back toward the retracted position.

The plunger 20 is further traversed to the engaged position. At the engaged position, the retraction forces of the internal and external variable vacuum compartments 62, 12 are sufficient to withdraw the needle holder 18 and needle 14 into the syringe body 16. Also, the lower surface 88 of the punch 86 of the piston 22 contacts the upper surface 90 of the retaining member 76. The punch 86 pushes the retaining member 76 off of the retaining surface 72 and about the releasing surface 74 thereby traversing the retaining member 76 from the first position to the second position. The lip 84 of the needle holder 18 and the inwardly directed flange 80 of the syringe body 16 prevent the needle holder 18 from being pushed out of the syringe body 16 through its distal portion. At about the time the retaining member 76 is traversed to the second position, the piston 22 engages the needle holder 18 via the longitudinal offset tabs 94 and the outwardly directed flange 92 of the needle holder 18. Any frictional force between the needle holder 18 and syringe body 16 and also between the piston 22, piston seal 56 and syringe body 16 may be less than the retraction forces of the external and/or internal variable vacuum compartments 12, 62. At the engaged position, the frusto conical cone 98 mates with the frusto conical surface 96 of the needle holder 18. Most of the fluidic medication is injected into the patient. The medical professional releases the thumb platform 26 and the retraction forces of the external and/or internal variable vacuum compartments 12, 62 urges the piston 22 as well as the needle holder 18 and needle 14 into the syringe body 16.

If the fluidic medication is not pre-filled into the variable fluid chamber 100, the medical professional may fill the variable fluid chamber 100 with fluidic medication. Initially, the retractable safety syringe 10 may be provided to the medical professional with the piston 22 in the retracted position. The medical professional may depress the thumb platform 26 to traverse the piston 22 to a filling position. The filling position is when the piston 22 is between the retracted position and the engaged position. Preferably, the filling position is when the piston 22 is closely adjacent to the needle holder 18 (see FIG. 4). By way of example and not limitation, the piston 22 may be characterized as being closely adjacent to the needle holder 18 when the piston 22 is closer to the needle holder 18 than the proximal portion of the syringe body 16 or the punch 86 of the piston 22 contacts the retaining member 76 and has not displaced the retaining member 76 off of the retaining surface 72. Once the piston 22 is in the filling position (i.e., piston adjacent the needle holder 18), the medical professional may insert the needle 14 into a medication container containing fluidic medication. The medical professional slowly releases pressure on the thumb platform 26 to permit the retraction forces of the external and/or internal variable vacuum compartments 12, 62 to traverse the piston 22 back toward the retracted position. As the piston 22 is traversed back toward the retracted position, fluidic medication inside of the medical container is transferred into the variable fluid chamber 100.

The medical professional may continue to release pressure on the thumb platform 26 until an appropriate amount of fluidic medication is contained in the variable fluid chamber 100. Optionally, the syringe body 16 may be fabricated from a clear material having volumetric graduations 102 (see FIG. 1) imprinted on an outer surface 36 of the syringe body 16. The medical professional may determine the amount of fluidic medication contained within the variable fluid chamber 100 by viewing the position of the piston 22 with respect to the volumetric graduation 102. When the appropriate amount of fluidic medication is contained within the variable fluid chamber 100, the medical professional removes the needle 14 from the medication container. The medical professional maintains thumb pressure on the thumb platform 26 such that air is not introduced into the variable fluid chamber 100. The medical professional inverts the needle 14 and taps the retractable safety syringe 10 to dislodge air bubbles within the variable fluid chamber 100 toward the needle 14 and depresses the thumb platform 26 to eject any air bubbles within the variable fluid chamber 100. The retractable safety syringe 10 is now prepared to inject the fluidic medication into the patient and may be injected into the patient via the steps discussed above.

The syringe 10 discussed herein provides for a sterile environment within the variable fluid chamber 100 such that fluidic medication filled within the variable fluid chamber 100 is not contaminated by the handling (e.g., touching outer surface 54 of plunger shaft 24) of the syringe 10 by the user or medical professional. The reason is that the proximal seal 30 is an airtight seal that prevents contaminates from entering the syringe body 16 (i.e., variable vacuum compartment 62) through its proximal portion. Moreover, the piston seal 56 provides an additional barrier to prevent contaminates from entering the variable fluid chamber 20 through the proximal portion of the syringe body 16. Furthermore, the rigid shell 28 provide for an additional barrier to contamination. The rigid shell 28 is disposed over shaft 24 such that a physical barrier exits between the outer surface 54 of the shaft 24 and the medical professional's fingers such that during use of the syringe 10, no contact is made with the medical professional and the outer surface 42 of the shaft 30.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A retractable safety syringe for preventing accidental needle pricking and needle reuse, the syringe comprising:
    a syringe body defining a distal portion and a proximal portion;
    a plunger disposed within the syringe body and extending through the proximal portion of the syringe body, the plunger being traverseable between a retracted position and an engaged position;
    a needle removeably engageable to the distal portion of the syringe body and engageable to the plunger when the plunger is traversed to the engaged position;
    a variable fluid chamber inside the syringe body, the variable fluid chamber located distally from the plunger, the variable fluid chamber having a distal and proximal end, the proximal end of the variable fluid chamber being sealed, the variable fluid chamber in fluid communication with the needle through the distal end of the variable fluid chamber and configured to be reduced in volume as the plunger is traversed toward the engaged position, and further configured so that a fluid medication contained in the variable fluid chamber is expelled from the variable fluid chamber through the needle when the plunger is traversed toward the engaged position;
    a shell attached to the plunger and disposed external to the syringe body, the shell and the syringe body defining a sealed external vacuum compartment wherein the external vacuum compartment is increased in volume as the plunger is traversed toward the engaged position creating a first retraction force; and
    wherein when the plunger engages the needle at the engaged position, the first retraction force of the external vacuum compartment traverses the needle into the syringe body.

2. The syringe of claim 1 wherein the syringe body defines an internal vacuum compartment isolated from the external vacuum compartment, wherein the internal vacuum compartment creates a second retraction force as the plunger is traversed toward the engaged position such that after the plunger engages the needle at the engaged position the first and second retraction forces of the internal and external vacuum compartments traverse the needle into the syringe body.

3. The syringe of claim 2 wherein the internal vacuum compartment is defined by the syringe body, a piston of the plunger, a piston seal disposed about the piston and a proximal seal attached to the proximal portion of the syringe body configured to provide an air tight seal between the syringe body and a shaft slidingly traverseable through the proximal seal.

4. The syringe of claim 1 wherein the external vacuum compartment is defined by the shell, the syringe body, a proximal seal attached to the proximal portion of the syringe body configured to form an air tight seal between an inner surface of the shell and the proximal portion of the syringe body, and a shell seal attached to a distal portion of the shell configured to form an air tight seal between the distal portion of the shell and an outer surface of the syringe body.

5. The syringe of claim 1 wherein the external vacuum compartment circumscribes the syringe body.

6. The syringe of claim 1 wherein the variable fluid chamber has a volume of about 1 cc or less when the plunger is fully retracted.

7. The syringe of claim 1 wherein the variable fluid chamber is pre filled with fluidic medication when supplied to a medical professional.

8. The syringe of claim 1 further comprising a carriage fixedly attached to the distal portion of the syringe body, the shell being slideably disposed within the carriage.

* * * * *